United States Patent [19]

Lowry

[11] Patent Number: 4,900,550

[45] Date of Patent: Feb. 13, 1990

[54] SKIN CARE COSMETIC REGIME

[75] Inventor: Edwina A. Lowry, Ada, Okla.

[73] Assignee: Amy Allene Cosmetiques, Inc., Ada, Okla.

[21] Appl. No.: 87,108

[22] Filed: Aug. 19, 1987

[51] Int. Cl.$^4$ .................. A61K 35/78; A61K 31/355; A61K 31/23
[52] U.S. Cl. ................................ 424/195.1; 514/458; 514/552; 514/725; 514/947
[58] Field of Search ............... 424/195.1, 81; 514/458, 514/725, 947, 552

[56] References Cited

U.S. PATENT DOCUMENTS

| | | | |
|---|---|---|---|
| 3,227,616 | 1/1966 | Van Wessem et al. | 514/738 |
| 4,268,526 | 5/1981 | Vargas et al. | 514/770 |
| 4,368,187 | 1/1983 | Flom et al. | 424/81 |

*Primary Examiner*—John W. Rollins
*Attorney, Agent, or Firm*—Laney, Dougherty, Hessin and Beavers

[57] ABSTRACT

A novel skin care cosmetic regime is disclosed which enhances the cell renewal cycle of skin without causing irritation. The regime comprises a softener component, a cell penetrating component, and a nourishment and protectant component. For less sensitive areas of skin, such as the hands, a sealant and tightening component is included in the regime.

8 Claims, No Drawings

SKIN CARE COSMETIC REGIME

BACKGROUND OF THE INVENTION

1. Field of the Invention

The present invention relates generally to cosmetics, and more particularly but not by way of limitation, to a skin care cosmetic regime and components used therein.

2. Brief Description of Prior Art

Skin care cosmetics, such as hand creams and lotions, have heretofore been employed to soften a person's skin, deter aging of the skin, and generally improve the overall health of the skin. Normal, healthy skin undergoes a natural renewal cycle wherein cells are constantly being produced or born, rise to the skin's surface through the epidermal layers, and then fall off. This renewal cycle for young skin is much more rapid than for mature skin. For example, healthy, young skin will normally renew itself every two weeks or so; whereas, healthy mature skin will renew itself about every four to six weeks.

In order to provide mature skin with a younger looking appearance, to retard aging spots and to soften the skin, it is desirable to accelerate the natural cell renewal cycle which results in the replacement of dead cells by new ones in the outer epidermal layer or stratum corneum. However, care must be exercised in accelerating the cell renewal cycle because irritation of the skin may occur due to the sloughing off of the dead stratum corneum cells, and such irritation may damage the skin.

The prior art is replete with cosmetic preparations, especially skin cream formulations and cell renewal cosmetic formulations for increasing the epidermal cell turnover without skin irritation. Typical of such prior art is as follows: Van Wessem et al., (U.S. Pat. No. 3,227,616); Sutliff et al., (U.S. Pat. No. 3,810,996); Hasunuma et al., (U.S. Pat. No. 4,000,276); Vargas et al., (U.S. Pat. No. 4,268,526); Cella et al., (U.S. Pat. No. 4,272,544); Flom et al., (U.S. Pat. No. 4,368,187); Herrold U.S. Pat. No. 4,581,230).

Many of the before-mentioned prior art references use a multiple component system containing components of various ingredients in the formulation of cosmetic preparations for use in a cosmetic skin regime. However, because of the concern for healthy and younger looking skin, especially as same relates to a person's hands and face, new and improved cosmetic preparations are constantly being sought which will accelerate the cell renewal cycles of mature skin without causing irritation. It is to such a cosmetic formulation and cosmetic regime that the subject invention is directed.

SUMMARY OF THE INVENTION

According to the present invention an improved and unique cosmetic formulation for use with a skin care cosmetic regime is provided for accelerating the cell renewal cycle of the skin to provide healthier, younger looking skin. The cosmetic formulations, which are employed in selective sequences in the skin care regime for sensitive skin, such as a person's face, include a softener component, a cell penetrating component, and a nourishment and protectant component. When utilizing the cosmetic formulations for less sensitive areas of the skin, such as a person's hands, the skin care regime further includes the application of a fourth component, namely, a sealant and skin tightener. Each of the components used in the skin care regime, and constituting the cosmetic formulations of the present invention, is formulated of specific ingredients to achieve the desired function in the conditioning of a person's skin.

An object of the present invention is to provide an improved skin care cosmetic formulation which increases epidermal cell turnover without irritation to the skin.

Another object of the present invention, while achieving before-stated object, is to provide an improved cosmetic formulation and skin care regime for the skin so as to deter aged spots, aging of the skin and generally improve the overall condition and health of the skin.

Other objects, advantages and features of the invention will be apparent from the following detailed description when read in conjunction with the appended claims.

DESCRIPTION

The skin care cosmetic formulations of the present invention comprise a plurality of components which are sequentially used in a skin care cosmetic regime. For example, when treating sensitive areas of the skin, such as the skin about a person's face, the skin care regime comprises application of a three component cosmetic formulation, namely, a softener component, a cell penetrating component and, a nourishment and protectant component. However, when employing the skin care cosmetic regime for treatment of less sensitive areas of he skin, such as the skin of a person's hands, it is desirable to include the regime the application of a fourth component, namely, a sealant and tightener component. In such instance the skin and tightener component is applied to the skin after the cell penetrating component and before application of the nourishment and protectant component.

The components of the skin care formulations of the present invention are prepared using specified ingredients, and are formulated using selected processing steps and conditions. The composition and formulation of each of the components is as follows:

SOFTENER COMPONENT

The softener component of the cosmetic preparation consists essentially of the following ingredients. It should be noted that the softener component is desirably used on extremely dry, rough skin of the body and is formulated to function as a massage vehicle. In formulating the softener composition that the amounts of the ingredients can vary within the ranges setforth, provided that the total weight percentages of the ingredients equal 100 weight percent of the softener component. Further, the column entitled "Experimental" is setforth as an example of a desired formulation of the softener component for use in the skin care regime of the present invention.

| Part | Softener Ingredients | Weight Percent | Experimental (Wt. %) |
|---|---|---|---|
| A | Aloe Concentrate | 8.75–10.50 | 9.70 |
|   | Propyl p-Hydroxybenzoate (Propyl Paraben) | 0.09–0.11 | .10 |
|   | Protopet (Petrolatum #15) | 75.00–80.00 | 79.31 |
|   | Octyl Palmitate | 2.20–3.30 | 3.00 |
|   | Safflower Oil | 0.90–1.30 | 1.00 |
|   | Cetyl Alcohol | 2.25–2.75 | 2.50 |
|   | Glyceryl Stearate & PEG 100 Stearate | 3.00– | 3.00 |

-continued

| Part | Softener Ingredients | Weight Percent | Experimental (Wt. %) |
|---|---|---|---|
| | (Lippocl L-4) | | |
| | Soluble Collagen | 0.40–0.55 | .50 |
| | Methyl p-Hydroxybenzoate (Methyl Paraben) | 0.09–0.11 | .10 |
| | Squalene | 1.35–1.65 | 1.50 |
| | Jojoba Oil | 0.18–0.22 | .20 |
| B | Vitamin E | 0.04–0.06 | .05 |
| | Vitamin A & D | 0.04–0.06 | .05 |
| | Colorant (FD & C Yellow #5) | qs | qs |
| | Fragrance (D-1030) | 0.01–0.03 | .02 |

The softener component of the cosmetic formulation is prepared as follows: The ingredients are weighed and the ingredients constituting Part A set forth above are added to a vat and heated to an elevated temperature (i.e. about 80° C.). The ingredients are constantly stirred during the heating phase. When the ingredients have reached the desired temperature, heat is removed and the ingredients are allowed to cool, while continuing agitation. When the ingredients have cooled to about 40° C. the ingredients constituting Part B above are added to the vat containing the ingredients of Part A while continuing to maintain agitation to insure a substantially uniform mixture of all the ingredients constituting the softener component. When the resulting mixture of the ingredients of Part A and Part B has cooled to ambient temperature, approximately 38° C., the resulting softener component is removed from the vat and placed into suitable containers or dispensers.

CELL PENETRATING COMPONENT

The cell penetrating component of the cosmetic preparation consists essentially of the following ingredients. The cell penetrating component is also recommended for use on very dry skin. In formulating the cell penetrating components the amounts of the ingredients can vary within the ranges setforth, provided that the total weight percentages of the ingredients equal 100 weight percent of the cell penetrating component. The column entitled "Experimental" is setforth as an example of a desired formulation of the cell penetrating component for use in the skin care regime of the present invention.

| Part | Cell Penetrating Ingredients | Weight Percent | Experimental (Wt. %) |
|---|---|---|---|
| A | Water | 0.45–0.55 | 0.50 |
| | Aloe Concentrate | 50.00–62.00 | 56.28 |
| | Triethanolamine | 0.70 | 0.70 |
| | Propylene Glycol | 2.70–3.30 | 3.00 |
| | Polysorbate 80 | 0.50 | 0.50 |
| | Tetrasodium Ethylenediaminetetra acetate (4NA EDTA Powder) | 0.09–0.11 | 0.10 |
| | Lanolin | 4.50–5.50 | 5.00 |
| | Stearic Acid | 3.00 | 3.00 |
| | Isopropyl Palmitate | 1.80–2.20 | 2.00 |
| | Glyceryl Sterate (GMS-450) | 1.50 | 1.50 |
| | Cetyl Alcohol | 0.45–0.55 | 0.50 |
| | Safflower Oil | 2.45–3.00 | 2.70 |
| | Methyl p-Hydroxybenzoate (Methyl Paraben) | 0.18–0.22 | 0.20 |
| | Propyl p-Hydroxybenzoate (Propyl Paraben) | 0.09–0.11 | 0.10 |
| | Cetyl Lactate | 0.40–0.55 | 0.50 |
| | Sweet Almond Oil | 0.09–0.11 | 0.10 |
| | Sunflower Oil | 0.09–0.11 | 0.10 |
| | Apricot Kernel Oil | 0.09–0.11 | 0.10 |
| | Sodium Pyroglutamic Carboxylic Acid (Sodium PCA) | 0.45–0.55 | 0.50 |
| | Vitamin E | 0.04–0.06 | 0.05 |
| | Allantoin | 0.04–0.06 | 0.05 |
| B | Carbopol 1.5% (Carbomer 940) | 22.00 | 22.00 |
| C | Collagen | 0.18–0.22 | 0.20 |
| | Elastin | 0.09–0.11 | 0.10 |
| | Hydrolyzed Mucopolysaccharides | 0.09–0.11 | 0.10 |
| | Hyaluronic Acid | 0.09–0.11 | 0.10 |
| D | Colorant (Red #33) | qs | qs |
| | Fragrance (D-1027) | 0.01–0.10 | 0.02 |

The cell penetrating component of the cosmetic formulation is prepared as follows: The ingredients are weighed and the ingredients constituting Part A setforth above are added to a vat and heated to an elevated temperature (i.e. about 75° C.). The ingredients are constantly stirred during the heating phase. Once the ingredients have reached the desired temperature, heat is removed and the ingredients are allowed to cool to about 40° C., while continuing stirring or agitation. The ingredients constituting Parts B, C, and D, are then sequentially added to the vat, while continuing to maintain agitation of the ingredients in the vat, until a substantially uniform mixture of the ingredients of Parts A, B, C, and D is obtained. Thereafter, the resulting mixture is allowed to cool to ambient temperature, approximately 38° C., removed from the vat, and placed in suitable containers or dispensers.

SEALANT AND SKIN TIGHTENER COMPONENT

The sealant and skin tightener component of the cosmetic preparation consists essentially of the following ingredients. It should be noted that the sealant and skin tightener component is not recommended, under normal circumstances, for use on sensitive areas of skin, (i.e. a person's face), but is recommended for use on less sensitive areas of the skin (i.e. a person's hands). Further, in formulating the sealant and skin tightener composition the amount of the ingredients can vary within the ranges setforth provided that the total weight percentages of the ingredients equal 100 weight percent of the sealant and skin tightener component. The column entitled "Experimental" is setforth as an example of a desired formulation of the sealant and skin tightener component for use in the skin care regime of the invention.

| Part | Sealant & Skin Tightener Ingredients | Weight Percent | Experimental (Wt. %) |
|---|---|---|---|
| A | Water | 41.00–51.00 | 45.98 |
| | Viscarin (Carrageenan) | 1.20 | 1.20 |
| | Aloe Vera Concentrate 50% | 0.40–0.60 | 0.50 |
| | Gum Arabic (Acacia) | 30.00–50.00 | 30.50 |
| | Corn Starch | 15.00–17.00 | 16.60 |
| | Tragacanth | 0.09–0.11 | 0.10 |
| | Locust Bean Gum | 0.09–0.11 | 0.10 |
| B | Titanium Dioxide (TiO$_2$) | 0.09–0.11 | 0.10 |
| | Propylene Glycol | 0.30–0.50 | 0.40 |
| | Polysorbate-80 | 2.70–3.30 | 3.00 |
| | TEA Lauryl Sulfate (TLS 40% ag) | 0.04–0.06 | 0.05 |

| Part | Sealant & Skin Tightener Ingredients | Weight Percent | Experimental (Wt. %) |
|---|---|---|---|
| | Inidazolidinyl Urea (Germall 115) | 0.90–1.10 | 1.00 |
| C | Hops, Rosemary, Horsepale, Pine & Lemon Extract (Phytelene 246) | 0.40–0.55 | 0.50 |
| | Colorant (2% DC Red #33 ag) | qs | qs |
| | Fragrance (D-S-335) | 0.20–0.30 | 0.25 |
| | Quaterinum 15 (Dowicil 200 Powder) | 0.09–0.11 | 0.10 |
| | Silk Amino Acid (hydrolyzed silk) | 0.09–0.10 | 0.10 |

The sealant and skin tightener component of the cosmetic formulation is prepared as follows: The ingredients are weighed and the water of Part A is added to a vat and heated to an elevated temperature (i.e. about 80? C.) while maintaining stirring or agitation. While continuing agitation, the remaining ingredients of Part A are admixed with the heated water and agitation is continued until the ingredients added are dispersed in the water and a substantially homogeneous mixture is formed. Thereafter, the ingredients of Part B are admixed with the heated homogeneous mixture formed of the ingredients of Part A. The rate of agitation is increased upon the mixture after the addition of the constitute of Part B, and the temperature is maintained until a smooth, substantially homogeneous mixture is formed containing the ingredients of Part A and Part B. Once the substantially homogeneous mixture is formed, heat is removed, while maintaining agitation and the homogeneous mixture is allowed to cool to ambient temperature (i.e. about 38° C.). After the mixture has cooled, the ingredients of Part C are admixed with the mixture and stirred until a homogeneous and uniform mixture is formed. The resulting mixture is then removed from the vat and placed into suitable containers or dispensers.

NOURISHMENT AND PROTECTANT COMPONENT

The nourishment and protectant component of the cosmetic preparation consists essentially of the following ingredients. It should be noted that in formulating the nourishment and protectant component that the amounts of the ingredients can vary within the ranges setforth, provided that the total weight percentages of the ingredients equal 100 weight percent of the nourishment and protectant component. The column entitled "Experimental" is set forth as an example of a desired formulation of the nourishment and protectant component for use in the skin care regime of the present invention.

| Part | Nourishment & Protectant Ingredients | Weight Percent | Experimental (Wt. %) |
|---|---|---|---|
| A | 50% Aloe Vera Solution | 57.00–60.00 | 57.87 |
| | Methyl p-Hydroxybenzoate (Methyl Paraben) | 0.18–0.22 | 0.20 |
| | Inidazolidinyl Urea (Germall 115) | 0.18–0.22 | 0.20 |
| | Propyl p-Hydroxybenzoate (Propyl Paraben) | 0.09–0.11 | 0.10 |
| | Stearic Acid | 10.00 | 10.00 |
| | Propylene Glycol | 15.25–16.50 | 15.50 |
| | Safflower Oil | 4.00–4.50 | 4.40 |
| | Homo Salicylate | 3.00 | 3.00 |
| | Apricot Kernel Oil | 0.10–0.50 | 0.10 |
| | 70% Sorbitol Soln | 3.45–4.20 | 3.85 |
| | Ceteth-4 | 2.00 | 2.00 |
| | White Protepet | 0.18–0.22 | 0.20 |
| | Wheat Germ Oil | 0.09–0.11 | 0.10 |
| | Jojoba Oil | 0.01–0.03 | 0.02 |
| | Panthenol (vitamin F) | 0.04–0.06 | 0.05 |
| | Vitamin A & D | 0.01–0.02 | 0.01 |
| | Vitamin E | 0.01–0.02 | 0.01 |
| | Triethanolamine 85% | 0.76 | 0.76 |
| | Fragrance (D 1045) | 0.02–0.10 | 0.03 |
| | Cetyl Lactate | 0.09–1.01 | 1.00 |
| | Sodium Pyroglutamic Carboxylic Acid (Sodium PCA) | 0.40–0.60 | 0.50 |
| B | Hydrolyzed Mucopolysaccharides | 0.09–0.11 | 0.10 |
| | Hyaluronic Acid | 0.05–0.10 | 0.05 |
| | Hydrolastin (Pentapharm) | 0.40–0.55 | 0.40 |
| | Liquid Collagen | 0.40–0.55 | 0.45 |
| | Colorant: | 0.03–0.07 | 0.05 |
| C | FD & C Yellow #5 | 0.01–0.03 | 0.02 |
| | FD & C Yellow #6 | 0.02–0.04 | 0.03 |

The nourishment and protectant component of the cosmetic formulation is prepared as follows: The ingredients are weighed, and thereafter the ingredients of part A are introduced into a vat and heated to a temperature of from about 70° to 93° C. The ingredients are constantly stirred during the heating phase, as well as during addition of the ingredients constituting Part B and C as will be setforth hereinafter. Once a substantially homogeneous mixture is formed at the temperature specified, the mixture is allowed to cool to about 30° C. Thereafter, the constitute of part B and C are admixed sequentially with the mixture formed of the ingredients of Part A and stirring is continued until a homogeneous mixture is obtained. The nourishment and protectant component so formed is removed from the vat and placed into suitable containers or dispensers.

In the cosmetic skin care regime employed for portions of the body having less sensitive areas of skin, such as a person's hand, foot, arm and the like (hereinafter referred to as "hands"), the first step of the regime is the application of an effective amount of the softener component to the hands to effectively cover the skin being treated. Once the softener component has been applied to the hands the skin is massaged for approximately two to three minutes, concentrating on dry, callus areas. When applied to the hands, attention should be paid to the cuticle area around the nails to insure softening of the cuticle area. Massaging of the skin is continued until the detected dry areas begin to soften. Once the softening of the dry areas of the skin on the hands is detected, the hands having the softener component thereon which has liquified as a result of the body temperature and the massaging action, are immersed in warm water and rinsed well to remove the softener component from the surface of the skin. Once rinsed, the skin is dried by any suitable means, such as by patting dry. It should be noted that because the top layer of skin is generally hard to penetrate, the softener is used to soften and prepare the skin to allow the other components of the cosmetic formulation used in the cosmetic skin care regime to penetrate and effectively assist in the cell renewal cycle of the skin. Further, the use of the softener removes undesired residue from the skin, such as dirt, oil and other impurities.

The second step of the cosmetic skin care regime is the application of the cell penetrating component to the hands cleaned with the softener component. A liberal amount of the cell penetrating component is massaged into the hands. The amount of the cell penetrating component applied will vary, depending on the condition of the skin. However, a sufficient amount of the cell penetrating component should be utilized so that after massaging the skin feels "slightly damp". The cell penetrating component is maintained on the skin (whether used in combination with the sealant and tightener component, as on non-sensitive areas of the skin, or without the use of the sealant and tightener component, as on sensitive areas of the skin) for a period of time effective to allow the cell penetrating component to penetrate the cell level of the skin, generally about 10 to 30 minutes.

When applied to non-sensitive areas of skin (i.e. the skin of a person's hands), the third step of the cosmetic skin care regime is the application of the sealant and tightener component to the hands having the cell penetrating component thereon. The sealant and tightener component seals the cell penetrating component and minimizes line formation. The sealant and tightener component can be applied to the hands with a brush, one's hands, or other suitable means, so that the hands are evenly covered in a "glove-like" application. To prevent the sealant and tightener component from attaching to hair on the arm and thereby pulling on the hair as it dries, a ring of the softener component is applied to the wrist prior to application of the sealant and tightener component.

Once the sealant and tightener component has been applied, the person is placed in a comfortable position so that the treated hands can be maintained in an undisturbed position for about 30 minutes to enable the sealant and tightener component to dry. The drying period can be shortened to about 10 minutes through the use of heated air, such as generated by a hair drier, or any other device capable of enhancing the drying of the sealant and tightener component.

Once the sealant and tightener component has dried, a small amount of warm water is applied to form a paste like material with the sealant and tightener component. Thereafter, additional water is applied, along with a massaging action. Finally, the hands are rinsed with warm water to remove any residual sealant and tightener component and dried.

The final step of the cosmetic skin care regime of the present invention is the application of the nourishment and protectant component. The nourishment and protectant component is applied to the hands and massaged into the skin until the amount which can be absorbed by the skin is indicated by a residual amount of the component on the skin. Thereafter, the skin is blotted with an absorbent material to remove the excess nourishment and protectant component from the surface of the skin.

The before-described cosmetic skin care regime employs a combination of unique components, each of which performs a specific function in the region. Further, use of the components in the skin care regime results in healthier skin, better looking skin and deters the formation of age spots as well as aging of the skin.

While presently preferred embodiments of the cosmetic skin care regime and components used therein have been described for the purpose of this disclosure, numerous changes may be made which will readily suggest themselves to those skilled in the art and which are encompassed within the spirit of the invention disclosed and as defined in the appended claims.

What is claimed is:

1. A method of accelerating cell renewal cycles of skin without causing irritation which comprises sequentially applying to the skin in a regime:

(a) initially, and in a first application step, a softener component consisting essentially of, in weight percent:

| Ingredients | Percentage |
| --- | --- |
| Aloe Concentrate | 8.75–10.50 |
| Propyl p-Hydroxybenzoate | 0.09–0.11 |
| Trotopet | 75.00–80.00 |
| Octyl Palmitate | 2.20–3.30 |
| Safflower Oil | 0.90–1.30 |
| Cetyl Alcohol | 2.25–2.75 |
| Glyceryl Stearate & PEG 100 Stearate | 3.00 |
| Soluble Collagen | 0.40–0.55 |
| Methyl p-Hydroxybenzoate | 0.09–0.11 |
| Squalene | 1.35–1.65 |
| Jojoba Oil | 0.18–0.22 |
| Vitamin E | 0.04–0.06 |
| Vitamin A & D | 0.04–0.06 |
| Colorant | qs |
| Fragrance | 0.01–0.03; |

(b) second, and in a second application step, a cell penetrating component consisting essentially of, in weight percent:

| Ingredients | Percentage |
| --- | --- |
| Water | 0.45–0.55 |
| Aloe Concentrate | 50.00–62.00 |
| Triethanolamine | 0.70 |
| Propylene Glycol | 2.70–3.30 |
| Polysorbate 80 | 0.50 |
| Tetrasodium Ethylenediaminetetra acetate | 0.09–0.11 |
| Lanolin | 4.50–5.50 |
| Stearic Acid | 3.00 |
| Isopropyl Palmitate | 1.80–2.20 |
| Glyceryl Sterate | 1.50 |
| Cetyl Alcohol | 0.45–0.55 |
| Safflower Oil | 2.45–3.00 |
| Methyl p-Hydroxybenzoate | 0.18–0.22 |
| Propyl p-Hydroxbenzoate | 0.09–0.11 |
| Cetyl Lactate | 0.40–0.55 |
| Sweet Almond Oil | 0.09–0.11 |
| Sunflower Oil | 0.09–0.11 |
| Apricot Kernel Oil | 0.09–0.11 |
| Sodium Pyroglutamic Carboxylic Acid | 0.45–0.55 |
| Vitamin E | 0.04–0.06 |
| Allantoin | 0.04–0.06 |
| Carbopol 1.5% | |
| Collagen | 0.18–0.22 |
| Elastin | 0.09–0.11 |
| Hydrolyzed Mucopolysaccharides | 0.09–0.11 |
| Hyaluronic Acid | 0.09–0.11 |
| Colorant | qs |
| Fragrance | 0.01–0.10; and |

(c) third, and as a third application step, a nourishment and protectant component consisting essentially of, in weight percent:

| Ingredients | Percentage |
| --- | --- |
| 50% Aloe Vera Solution | 57.00–60.00 |
| Methyl p-Hydroxybenzoate | 0.18–0.22 |
| Iniduzolidinyl Urea | 0.18–0.22 |
| Propyl p-Hydroxybenzoate | 0.09–0.11 |
| Stearic Acid | 10.00 |
| Propylene Glycol | 15.25–16.00 |

-continued

| Ingredients | Percentage |
|---|---|
| Safflower Oil | 4.00–4.50 |
| Homo Salicylate | 3.00 |
| Apricot Kernel Oil | 0.10–0.50 |
| 70% Sorbitol Solution | 3.45–4.20 |
| Ceteth-4 | 2.00 |
| White Protepet | 0.18–0.22 |
| Wheat Germ Oil | 0.09–0.11 |
| Jojoba Oil | 0.01–0.03 |
| Panthenol (vitamin F) | 0.04–0.06 |
| Vitamin A & D | 0.01–0.02 |
| Vitamin E | 0.01–0.02 |
| Triethanolamine 85% | .76 |
| Fragrance | 0.02–0.10 |
| Cetyl Lactate | 0.09–1.01 |
| Sodium Pyroglutamic Carboxylic Acid | 0.40–0.60 |
| Hydrolyzed Mucopolysaccharides | 0.09–0.11 |
| Hyaluronic Acid | 0.05–0.10 |
| Hydrolastin | 0.40–0.55 |
| Liquid Collagen | 0.45–0.55 |
| Colorant. | |

2. The method of accelerating cell renewal cycles of skin according to claim 1 wherein said regime further comprises:
(d) a sealant and tightener component applied to said skin after the cell penetrating component of (b) and prior to the nourishment and protectant component of (c), said sealant and tightener component consisting essentially of, in weight percent:

| Ingredients | Percentage |
|---|---|
| Water | 41.00–51.00 |
| Viscarin | 1.20 |
| Aloe Vera Concentrate 50% | 0.40–0.60 |
| Gum Arabic | 30.00–50.00 |
| Corn Starch | 15.00–17.00 |
| Tragacanth | 0.09–0.11 |
| Locust Bean Gum | 0.09–0.11 |
| Titanium Dioxide | 0.09–0.11 |
| Propylene Glycol | 0.30–0.50 |
| Polysorbate-80 | 2.70–3.30 |
| TEA Lauryl Sulfate | 0.04–0.06 |
| Inidazolidinyl Urea | 0.90–1.10 |
| Mixture of Hops, Rosemary, Horsepale, Pine & Lemon Extract | 0.40–0.55 |
| Colorant | qs |
| Fragrance | 0.20–0.30 |
| Quaterinum 15 | 0.09–0.11 |
| Silk Amino Acid | 0.09–0.10 |

3. A softener component for cleansing and softening skin, said softener component consisting essentially of, in percentage by weight:

| Ingredients | Percentage |
|---|---|
| Aloe Concentrate | 8.75–10.50 |
| Propyl p-Hydroxybenzoate | 0.09–0.11 |
| Trotopet | 75.00–80.00 |
| Octyl Palmitate | 2.20–3.30 |
| Safflower Oil | 0.90–1.30 |
| Cetyl Alcohol | 2.25–2.75 |
| Glyceryl Stearate & PEG 100 Stearate | 3.00 |
| Soluble Collagen | 0.40–0.55 |
| Methyl p-Hydroxybenzoate | 0.09–0.11 |
| Squalene | 1.35–1.65 |
| Jojoba Oil | 0.18–0.22 |
| Vitamin E | 0.04–0.06 |

-continued

| Ingredients | Percentage |
|---|---|
| Vitamin A & D | 0.04–0.06 |
| Colorant | qs |
| Fragrance | 0.01–0.03; |

4. A cell penetrating component for application to skin to accelerate cell renewal of the skin, said cell penetrating component consisting essentially of, in percentage by weight:

| Ingredients | Percentage |
|---|---|
| Water | 0.45–0.55 |
| Aloe Concentrate | 50.00–62.00 |
| Triethanolamine | 0.70 |
| Propylene Glycol | 2.70–3.30 |
| Polysorbate 80 | 0.50 |
| Tetrasodium Ethylenediaminetetra acetate | 0.09–0.11 |
| Lanolin | 4.50–5.50 |
| Stearic Acid | 3.00 |
| Isopropyl Palmitate | 1.80–2.20 |
| Glyceryl Sterate | 1.50 |
| Cetyl Alcohol | 0.45–0.55 |
| Safflower Oil | 2.45–3.00 |
| Methyl p-Hydroxybenzoate | 0.18–0.22 |
| Propyl p-Hydroxbenzoate | 0.09–0.11 |
| Cetyl Lactate | 0.40–0.55 |
| Sweet Almond Oil | 0.09–0.11 |
| Sunflower Oil | 0.09–0.11 |
| Apricot Kernel Oil | 0.09–0.11 |
| Sodium Pyroglutamic Carboxylic Acid | 0.45–0.55 |
| Vitamin E | 0.04–0.06 |
| Allantoin | 0.04–0.06 |
| Carbopol 1.5% Collagen | 0.18–0.22 |
| Elastin | 0.09–0.11 |
| Hydrolyzed Mucopolysaccharides | 0.09–0.11 |
| Hyaluronic Acid | 0.09–0.11 |
| Colorant | qs |
| Fragrance | 0.01–0.10; and |

5. A nourishment and protectant component for use in skin care, said nourishment and protectant component consisting essentially of, in percent by weight:

| Ingredients | Percentage |
|---|---|
| 50% Aloe Vera Solution | 57.00–60.00 |
| Methyl p-Hydroxybenzoate | 0.18–0.22 |
| Iniduzolidinyl Urea | 0.18–0.22 |
| Propyl p-Hydroxybenzoate | 0.09–0.11 |
| Stearic Acid | 10.00 |
| Propylene Glycol | 15.25–16.00 |
| Safflower Oil | 4.00–4.50 |
| Homo Salicylate | 3.00 |
| Apricot Kernel Oil | 0.10–0.50 |
| 70% Sorbitol Solution | 3.45–4.20 |
| Ceteth-4 | 2.00 |
| White Protepet | 0.18–0.22 |
| Wheat Germ Oil | 0.09–0.11 |
| Jojoba Oil | 0.01–0.03 |
| Panthenol (vitamin F) | 0.04–0.06 |
| Vitamin A & D | 0.01–0.02 |
| Vitamin E | 0.01–0.02 |
| Triethanolamine 85% | .76 |
| Fragrance | 0.02–0.10 |
| Cetyl Lactate | 0.09–1.01 |
| Sodium Pyroglutamic Carboxylic Acid | 0.40–0.60 |
| Hydrolyzed Mucopolysaccharides | 0.09–0.11 |
| Hyaluronic Acid | 0.05–0.10 |
| Hydrolastin | 0.40–0.55 |

| Ingredients | Percentage |
| --- | --- |
| Liquid Collagen | 0.45–0.55 |
| Colorant. | |

6. A sealant and skin tightener component consisting essentially of, in percent by weight:

| Ingredients | Percentage |
| --- | --- |
| Water | 41.00–51.00 |
| Viscarin | 1.20 |
| Aloe Vera Concentrate 50% | 0.40–0.60 |
| Gum Arabic | 30.00–50.00 |
| Corn Starch | 15.00–17.00 |
| Tragacanth | 0.09–0.11 |
| Locust Bean Gum | 0.09–0.11 |
| Titanium Dioxide | 0.09–0.11 |
| Propylene Glycol | 0.30–0.50 |
| Polysorbate-80 | 2.70–3.30 |
| TEA Lauryl Sulfate | 0.04–0.06 |
| Inidazolidinyl Urea | 0.90–1.10 |
| Mixture of Hops, Rosemary, Horsepale, Pine & Lemon Extract | 0.40–0.55 |
| Colorant | qs |
| Fragrance | 0.20–0.30 |
| Quaterinum 15 | 0.09–0.11 |
| Silk Amino Acid | 0.09–0.10 |

7. A cosmetic skin care method for enhancing skin cell renewal, said regime comprising:
   (a) applying an amount of a softener component to a portion of skin to be treated to effectively cover said portion of skin, said softener component consisting essentially of, in percentage by weight:

| Ingredients | Percentage |
| --- | --- |
| Aloe Concentrate | 8.75–10.50 |
| Propyl p-Hydroxybenzoate | 0.09–0.11 |
| Trotopet | 75.00–80.00 |
| Octyl Palmitate | 2.20–3.30 |
| Safflower Oil | 0.90–1.30 |
| Cetyl Alcohol | 2.25–2.75 |
| Glyceryl Stearate & PEG 100 Stearate | 3.00 |
| Soluble Collagen | 0.40–0.55 |
| Methyl p-Hydroxybenzoate | 0.09–0.11 |
| Squalene | 1.35–1.65 |
| Jojoba Oil | 0.18–0.22 |
| Vitamin E | 0.04–0.06 |
| Vitamin A & D | 0.04–0.06 |
| Colorant | qs |
| Fragrance | 0.01–0.03; |

(b) massaging said skin covered with the softener component for a period of time effective to soften said skin;
   (c) removing said softener component from the skin so as to provide a substantially dry cleaned skin;
   (d) applying an amount of a cell penetrating component to the dry cleaned skin to effectively cover the skin and provide the skin with a damp feel, said cell penetrating component consisting essentially of, in percentage by weight:

| Ingredients | Percentage |
| --- | --- |
| Water | 0.45–0.55 |
| Aloe Concentrate | 50.00–62.00 |
| Triethanolamine | 0.70 |
| Propylene Glycol | 2.70–3.30 |
| Polysorbate 80 | 0.50 |
| Tetrasodium Ethylenediaminetetra acetate | 0.09–0.11 |
| Lanolin | 4.50–5.50 |
| Stearic Acid | 3.00 |
| Isopropyl Palmitate | 1.80–2.20 |
| Glyceryl Sterate | 1.50 |
| Cetyl Alcohol | 0.45–0.55 |
| Safflower Oil | 2.45–3.00 |
| Methyl p-Hydroxybenzoate | 0.18–0.22 |
| Propyl p-Hydroxbenzoate | 0.09–0.11 |
| Cetyl Lactate | 0.40–0.55 |
| Sweet Almond Oil | 0.09–0.11 |
| Sunflower Oil | 0.09–0.11 |
| Apricot Kernel Oil | 0.09–0.11 |
| Sodium Pyroglutamic Carboxylic Acid | 0.45–0.55 |
| Vitamin E | 0.04–0.06 |
| Allantoin | 0.04–0.06 |
| Carbopol 1.5% | |
| Collagen | 0.18–0.22 |
| Elastin | 0.09–0.11 |
| Hydrolyzed Mucopolysaccharides | 0.09–0.11 |
| Hyaluronic Acid | 0.09–0.11 |
| Colorant | qs |
| Fragrance | 0.01–0.10; and |

(e) massaging the cell penetrating component covered portion of the skin for a period of time effective to allow the cell penetrating component to penetrate the cell level of the skin; and
   (f) applying an effective amount of a nourishment and protectant component to the skin treated with the cell penetrating component, said effective amount being the amount absorbable by the skin, said nourishment and protectant component consisting essentially of, in percent by weight:

| Ingredients | Percentage |
| --- | --- |
| 50% Aloe Vera Solution | 57.00–60.00 |
| Methyl p-Hydroxybenzoate | 0.18–0.22 |
| Iniduzolidinyl Urea | 0.18–0.22 |
| Propyl p-Hydroxybenzoate | 0.09–0.11 |
| Stearic Acid | 10.00 |
| Propylene Glycol | 15.25–16.00 |
| Safflower Oil | 4.00–4.50 |
| Homo Salicylate | 3.00 |
| Apricot Kernel Oil | 0.10–0.50 |
| 70% Sorbitol Solution | 3.45–4.20 |
| Ceteth-4 | 2.00 |
| White Protepet | 0.18–0.22 |
| Wheat Germ Oil | 0.09–0.11 |
| Jojoba Oil | 0.01–0.03 |
| Panthenol (vitamin F) | 0.04–0.06 |
| Vitamin A & D | 0.01–0.02 |
| Vitamin E | 0.01–0.02 |
| Triethanolamine 85% | .76 |
| Fragrance | 0.02–0.10 |
| Cetyl Lactate | 0.09–1.01 |
| Sodium Pyroglutamic Carboxylic Acid | 0.40–0.60 |
| Hydrolyzed Mucopolysaccharides | 0.09–0.11 |
| Hyaluronic Acid | 0.05–0.10 |
| Hydrolastin | 0.40–0.55 |
| Liquid Collagen | 0.45–0.55 |
| Colorant. | |

8. The cosmetic skin care method of claim 7 further comprising:
   (g) applying an amount of a sealant and tightener component to the skin effective to cover the skin, said sealant and tightener component being applied to the skin after massaging the cell penetrating component covered skin of step (e), said sealant and tightener component consisting essentially of, in percent by weight:

| Ingredients | Percentage |
| --- | --- |
| Water | 41.00–51.00 |
| Viscarin | 1.20 |
| Aloe Vera Concentrate 50% | 0.40–0.60 |
| Gum Arabic | 30.00–50.00 |
| Corn Starch | 15.00–17.00 |
| Tragacanth | 0.09–0.11 |
| Locust Bean Gum | 0.09–0.11 |
| Titanium Dioxide | 0.09–0.11 |
| Propylene Glycol | 0.30–0.50 |
| Polysorbate-80 | 2.70–3.30 |
| TEA Lauryl Sulfate | 0.04–0.06 |
| Inidazolidinyl Urea | 0.90–1.10 |
| Mixture of Hops, Rosemary, Horsepale, Pine & Lemon Extract | 0.40–0.55 |
| Colorant | qs |
| Fragrance | 0.20–0.30 |
| Quaterinum 15 | 0.09–0.11 |
| Silk Amino Acid | 0.09–0.10 |

(h) maintaining said sealant and tightener composition on said skin for a period of time effective to allow same to dry; and (i) rinsing said dried sealant and tightener composition from said skin while simultaneously massaging said skin.

* * * * *

UNITED STATES PATENT AND TRADEMARK OFFICE
CERTIFICATE OF CORRECTION

PATENT NO. : 4,900,550
DATED : February 13, 1990
INVENTOR(S) : Edwina A. Lowry

It is certified that error appears in the above-identified patent and that said Letters Patent is hereby corrected as shown below:

In Column 2, line 29, delete "he" and insert -the-.
In Column 5, line 18, delete "80?" and insert -80°-.

Signed and Sealed this

Fifteenth Day of January, 1991

*Attest:*

HARRY F. MANBECK, JR.

*Attesting Officer*  *Commissioner of Patents and Trademarks*